United States Patent [19]

Smith

[11] 4,274,846
[45] Jun. 23, 1981

[54] PARTICLE SIZING SAMPLER

[75] Inventor: Michael L. Smith, Atlanta, Ga.

[73] Assignee: Andersen Samplers Inc., Atlanta, Ga.

[21] Appl. No.: 13,401

[22] Filed: Feb. 21, 1979

[51] Int. Cl.³ .............................................. B01D 53/30
[52] U.S. Cl. ...................................... 55/270; 55/319;
 55/446; 55/465; 73/28
[58] Field of Search .......... 55/189, 194, 319, 257 NP,
 55/482, 270, 325, 337, 446, 465–466; 73/421.5
 R, 28, 29, 432 TS

[56] References Cited

U.S. PATENT DOCUMENTS

| 2,538,116 | 6/1951 | May | 73/28 |
|---|---|---|---|
| 3,001,914 | 9/1961 | Anderson | 73/28 |
| 3,530,649 | 9/1970 | Porsch et al. | 55/325 |
| 3,606,738 | 9/1971 | Kraus, Jr. | 55/446 |
| 3,614,862 | 10/1971 | Connors | 55/337 |
| 3,616,625 | 11/1971 | Everett et al. | 55/465 X |
| 3,693,457 | 9/1972 | Pilat | 55/465 X |
| 3,710,557 | 1/1973 | Couchman et al. | 55/270 |
| 3,795,135 | *3/1974 | Anderson | 73/28 |
| 3,802,167 | 4/1974 | Turman | 55/337 |
| 3,917,472 | 11/1975 | Berz | 55/337 |
| 3,953,182 | 4/1976 | Roth | 73/28 X |

FOREIGN PATENT DOCUMENTS

| 565256 | 7/1957 | Italy | 55/465 |
|---|---|---|---|
| 7612092 | 5/1978 | Netherlands | 55/186 |

*Primary Examiner*—Charles N. Hart
*Assistant Examiner*—E. Rollins Cross
*Attorney, Agent, or Firm*—B. J. Powell

[57] ABSTRACT

A particle sizing sampling device to separate particles from a gaseous medium according to particle diameter so as to classify the particles which include one or more stages with a housing defining an impaction chamber therein, an impaction plate in the impaction chamber, at least one impaction nozzle which forces a jet of the gaseous medium against the impaction plate to separate those particles above the effective particle cut diameter of the stage of the sampler by jet impaction and at least one exit passage which extends through the impaction plate with an inlet spaced from the impaction plate a distance greater than the distance between the gas jet stream outlet from the impaction nozzle and the impaction plate.

13 Claims, 15 Drawing Figures

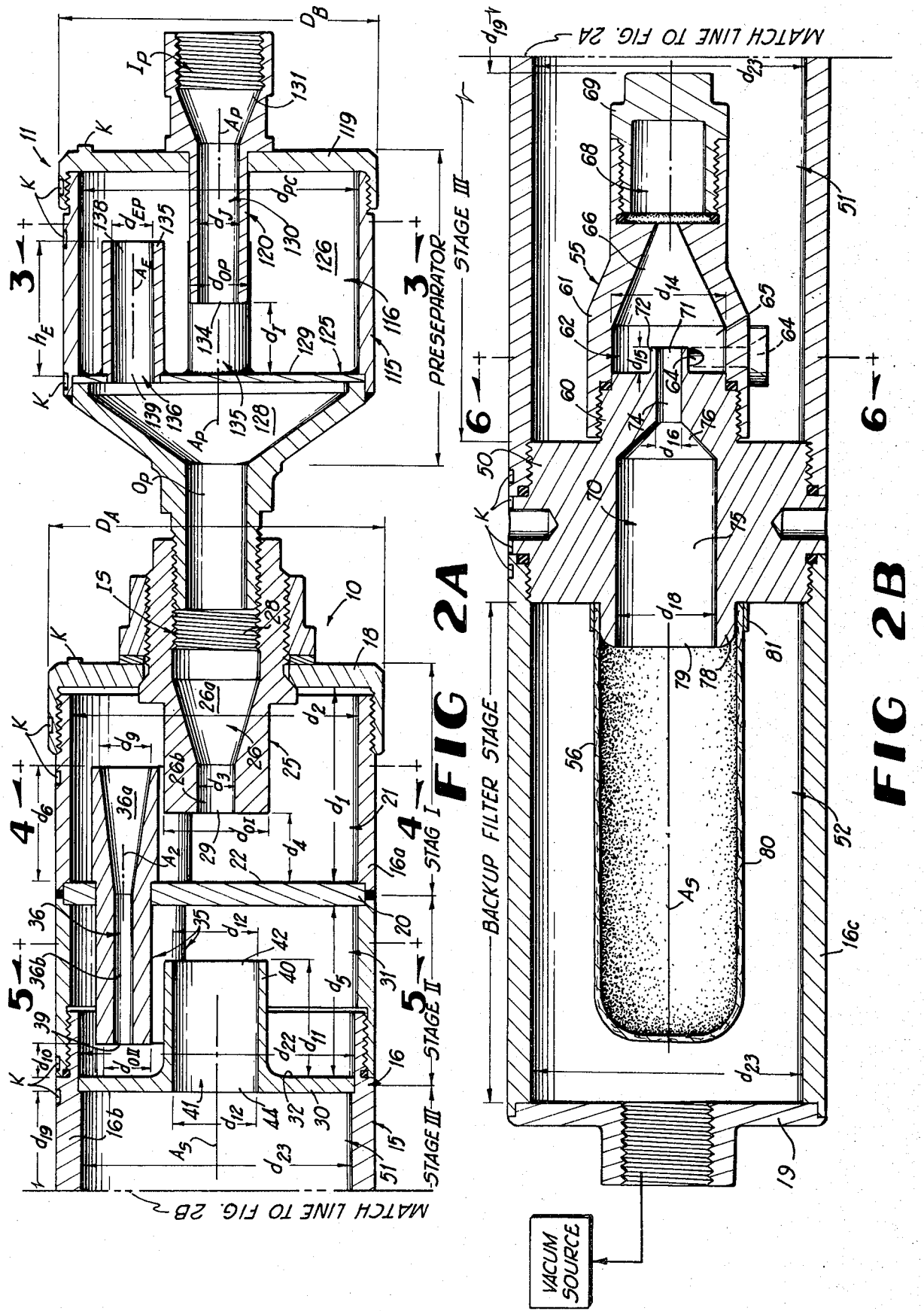

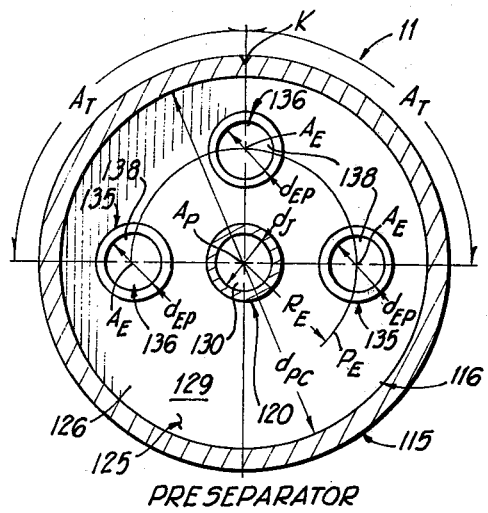
FIG 3 PRESEPARATOR
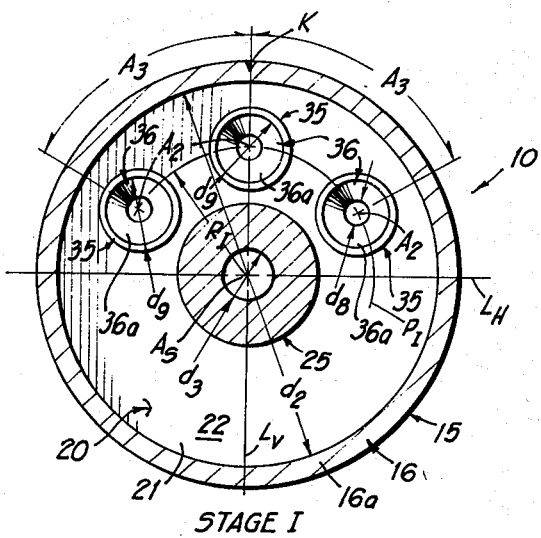
FIG 4 STAGE I
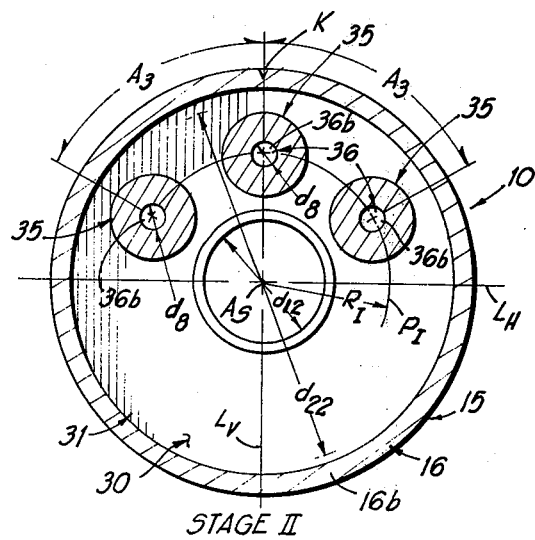
FIG 5 STAGE II
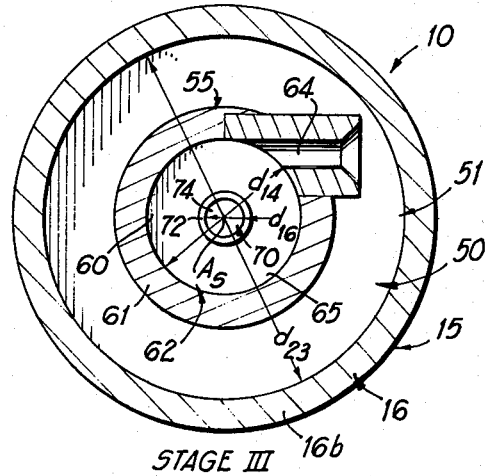
FIG 6 STAGE III

PARTICLE SIZING SAMPLER

BACKGROUND OF THE INVENTION

Various particle sizing samplers are available on the market today for sampling, according to size, particulate pollutants entrained in a gaseous medium such as air or stack gases. These samplers are generally of two different types, the jet impaction type sampler and the cyclone type sampler. The jet impaction type sampler serially directs jets of the gaseous medium against impaction surfaces at different velocities in ascending sequence so that different size particles are separated at the different velocities. The cyclone type sampler uses a series of cyclones through which the gaseous medium serially passes with each cyclone separating different size particles. Both of these types of sampler suffer from certain problems.

One of the problems associated with prior art jet impaction type particle sizing samplers is that such samplers generally have a capability of collecting and sizing only small quantities of particles from the gaseous medium without the particles which already have been collected by jet impaction being reentrained in the gaseous medium. When this occurs, of course, the sizing accuracy of the sampler deteriorates, thereby making it difficult to determine what size particles were collected from the gaseous medium. Because the particle concentrations in gas streams which are being sampled vary widely, the jet impaction type sampler is frequently unable to take a sample of the gaseous medium for the necessary length of time to conduct proper sampling in gas streams with high particle concentrations.

One of the problems associated with cyclone type samplers is that, at any given volumetric flow rate, a particular size cyclone has to be associated with each particle size to be collected since the size of the cyclone itself determines the size of the particles which are collected by that cyclone. As a result, the physical arrangement of the cyclones in the sampler is difficult to achieve while at the same time keeping the overall sampler size small enough to fit through the standard sampling ports which are normally available in ducts carrying the gaseous medium. An even greater problem with cyclones is that there is no satisfactory theoretical formulation from which to predict the particle size which a cyclone will collect at various combinations of pressure and temperature. Eacy cyclone must be calibrated empirically at the possible combinations of gas temperature and gas pressure which might be encountered in actual field use. This calibration procedure is expensive and subject to errors. Another problem which has been encountered with cyclone type samplers is that some of the particles may be removed from the gaseous medium within the complex passage arrangements required to interconnect the different cyclones rather than at the desired collection points in the cyclones. This causes inaccurate results in the indicated particle size distribution in the gaseous medium. Yet another problem encountered with the cyclone type sampler is that some of the separated particles may be reentrained in the gaseous medium to thereby reduce the collection size accuracy of the sampler.

SUMMARY OF THE INVENTION

Many of the problems and disadvantages associated with prior art particle sizing samplers are overcome and the remaining problems are minimized by the invention disclosed herein by providing a particle sizing sampler which has the capability of separating large quantities of particles from the gaseous medium being sampled with minimal reentrainment while at the same time being small enough to fit through the standard size access ports which are normally available in the ducts carrying the gaseous medium. Further, the gas flow path through the sampler minimizes the particles being separated at locations in the sampler other than those at which accurate measurements of the particle size can be achieved.

The apparatus of the invention is a particle sizing sampling device which separates particles from a gaseous medium according to particle diameter so as to classify the particles. The sampling device includes one or more stages through which the gaseous medium is passed serially with each of the stages separating smaller size particles from the gaseous medium than the next upstream stage. The sampling device includes a housing which defines an impaction chamber therein with an impaction surface located in the impaction chamber and an impaction nozzle means which defines at least one impaction jet passage therethrough which is oriented normal to the impaction surface in the impaction chamber so that the jet stream of the gaseous medium issuing from the impaction jet passage impinges on the impaction surface to cause those particles in the gaseous medium with effective particle diameters above a prescribed effective particle cut diameter to be separated on the impaction surface by jet impaction when the gaseous medium is appropriately forced through the impaction jet passage. At least one exit passage is provided from the impaction chamber through which the gaseous medium passes from the impaction chamber. The inlet to the exit passage is spaced from the impaction surface a distance greater than that of the jet outlet on the jet impaction passage so that the gaseous medium turns away from the impaction surface in the impaction chamber to move to the inlet of the exit passage for passage out of the impaction chamber. Gas forcing means such as a vacuum pump are appropriately connected to the sampling device to force the gaseous medium through the sampling device to separate the particles from the gas stream according to size. The size of the impaction chamber is such that the velocity of the gas stream in the impaction chamber is less than one tenth of the velocity of the gas stream as it exits the impaction jet passage in the impaction nozzle means and the total inlet area to the exit passage is at least two times the total cross-sectional area of the impaction jet passage in the impaction nozzle means. The sampling device may be arranged in first and second jet impaction stages, a third cyclone stage, and a fourth backup filter stage. The impaction chambers in the impaction stages may be arranged so that the major gas flow through the impaction chamber occupies an upper portion of the impaction chamber so that any particles which agglomerate and fall away from the point of impaction can fall to the lower portion of the impaction chamber out of the gas stream flow.

These and other features and advantages of the invention disclosed herein will become more apparent upon consideration of the following specifications and accompanying drawings wherein like characters of reference designate corresponding parts throughout the several views and in which:

BRIEF DESCRIPTION OF THE DRAWINGS

FIGS. 2a and 2b together form an enlarged longitudinal cross-sectional view of that embodiment of the invention in FIG. 1;

FIG. 3 is a transverse cross-sectional view taken generally along the line 3—3 in FIG. 2a;

FIG. 4 is a transverse cross-sectional view taken generally along the line 4—4 in FIG. 2a;

FIG. 5 is a transverse cross-sectional view taken generally along the line 5—5 in FIG. 2a;

FIG. 6 is a transverse cross-sectional view taken generally along line 6—6 in FIG. 2b.

FIG. 11 is a transverse cross-sectional view taken generally along the line 11—11 in FIG. 10a;

FIG. 12 is a transverse cross-sectional view taken generally along the line 12—12 in FIG. 10a; and, FIG. 13 is a transverse cross-sectional view taken generally along the line 13—13 in FIG. 10a.

Figure 1:
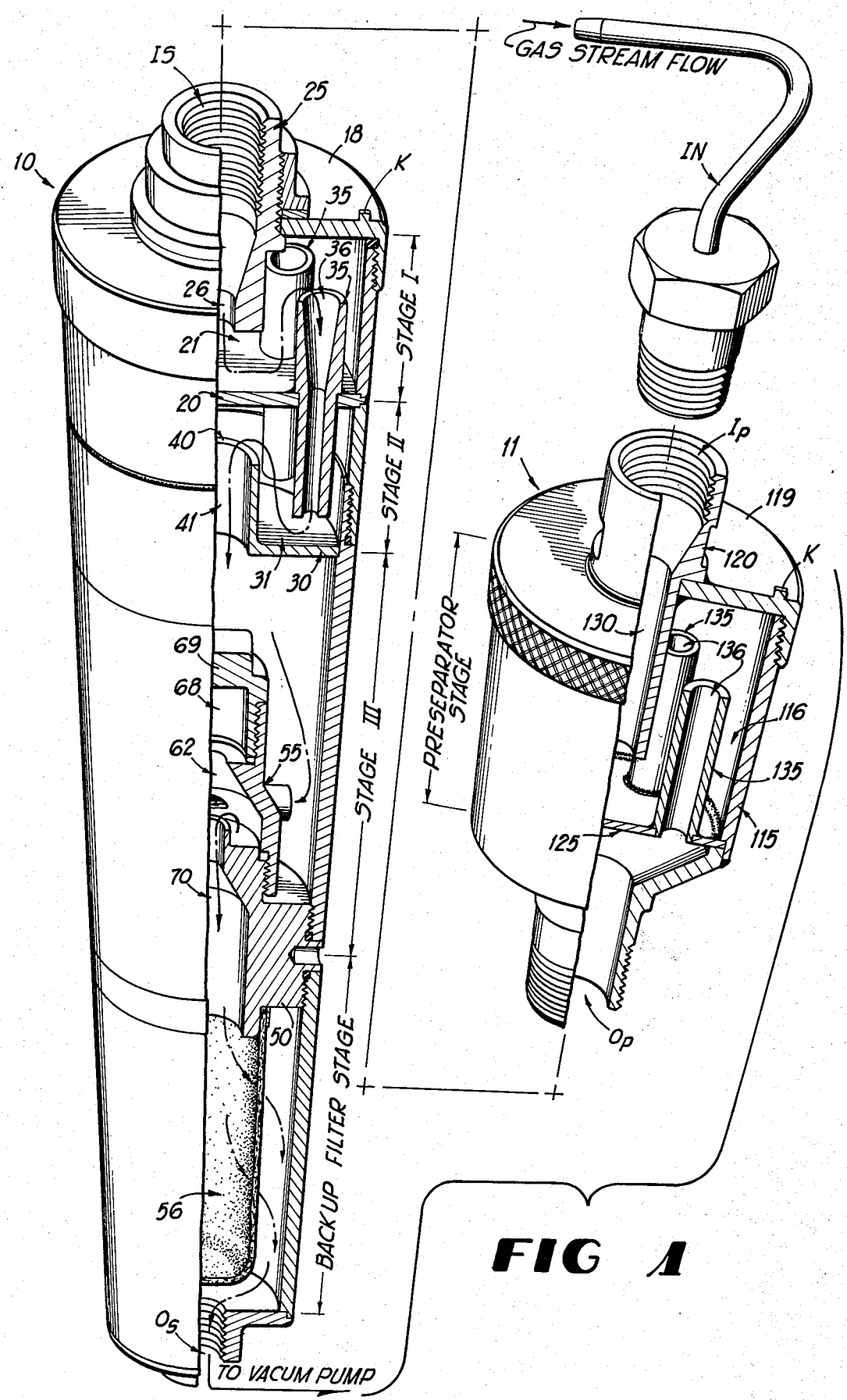
FIG. 1 is an exploded perspective view partially shown in section of the invention.

These figures and the following detailed description disclose specific embodiments of the invention; however, it is to be understood that the inventive concept is not limited thereto since it may be embodied in other forms.

DETAILED DESCRIPTION OF ILLUSTRATIVE EMBODIMENTS

Referring to the FIGS. 1–8, it will be seen that a first embodiment of the invention is incorporated in a particle sizing sampler 10 which may be used in combination with a particle sizing preseparator 11 if sampling of gas streams with large size particles is being conducted. The sampler 10 has a sampler central axis $A_S$ which is generally coaxially arranged with the preseparator central axis $A_P$. The particle sizing sampler 10 has an inlet $I_S$ and an outlet $O_S$ while the preseparator 11 has an outlet $O_P$ and an inlet $I_P$. Normally, the sampler outlet $O_S$ is connected to a vacuum pump as is well known in the sampler art while the outlet $O_P$ of the preseparator 11 is connected to the inlet $I_S$ of the sampler 10. The inlet $I_P$ of the preseparator 11 is generally connected to an inlet nozzle IN seen in FIG. 1 as a gooseneck nozzle so that when the sampler 10 and preseparator 11 are assembled and inserted into the gas stream, the inlet opening of the gooseneck nozzle IN faces the oncoming gas stream with its inlet axis generally parallel to the gas stream flow. The sample of the gaseous medium taken in through the inlet nozzle IN passes generally axially through the preseparator 11 and sampler 10 and then out through the vacuum pump. Both the sampler 10 and preseparator 11 are designed to operate most effectively in high particle loading conditions while the axes $A_S$ and $A_P$ are generally horizontal and with the top edge of the sampler 10 and preseparator 11 as indicated by the indicia K uppermost as will become more apparent. If the gas stream being sampled does not have the larger size particles requiring the use of preseparator 11, it may be removed and the inlet nozzle IN fitted directly onto the inlet $I_S$ of sampler 10.

The particle sizing sampler 10 is designed to divide those size particles entrained in the gaseous medium which are sufficiently small to (1) represent a health hazard, (2) be difficult to remove from the gas stream with pollution control equipment, and (3) disperse over a wide area once released into the atmosphere. The particle sizes which penetrate the human respiratory system have been found to be those generally below about 10 microns in diameter. Particles smaller than approximately 5 microns become increasingly difficult to remove from the gas stream and those particles smaller than approximately 2 microns will disperse over a wide area once released into the atmosphere. The particle sizing sampler 10 separates those particles which lie generally below the 11 micron size range according to size. The particle sizing sampler 10 may have any desired number of stages; however, the particle sizing sampler illustrated has four stages: Stage I, Stage II, Stage III, and a Backup Filter Stage. Under standard operating conditions as will become more apparent, Stage I is designed to have an effective particle cut diameter of about 11 microns; Stage II is designed to have an effective particle cut diameter of about 6 microns; Stage III is designed to have an effective particle cut diameter of about 1.5 microns; and the Backup Filter Stage is designed to remove all of the particles remaining in the gas stream after passage through Stage III. Stages I and II operate by jet impaction while Stage III is a cyclone and the Backup Stage is an absolute filter. Stage III could likewise operate by jet impaction.

The particle sizing sampler 10 includes generally a cylindrical housing 15 in which is mounted all four of the stages of the sampler. The cylindrical housing 15 includes generally a tubular cylindrical side wall 16 which is divided into sections 16a–16c that are selectively threaded together so that the different stages can be disassembled to permit the collected sample to be examined. It is to be understood, however, that the sampler housing 15 may be appropriately made so that the stages all fit within the sampler housing 15 without having to disassemble the side wall 16. The section 16a of the side wall 16 at the inlet end of the sampler 10 is closed by an end cap 18 threadedly connected to the section 16a so that it can be removed while the outlet end of the housing 15 is closed by an end plate 19 welded to the end of section 16c. The housing 15 has a maximum transverse cross-sectional diameter $D_A$ sized so that the housing 15 will pass through the standard access ports conventionally provided in the ducts carrying the gaseous medium. This standard size is usually about 3 inches (7.62 cm) for the access ports so that diameter $D_A$ is less than 3 inches (7.62 cm).

A circular first stage impaction plate 20 (FIGS. 2A and 4) is mounted in the section 16a of side wall 16 a distance $d_1$ (FIG. 2A) downstream of end cap 18. Plate 20 is oriented normal to the sampler axis $A_S$ and forms a first stage impaction chamber 21 of diameter $d_2$ (FIG. 4) bounded by side wall 16, end cap 18 and plate 20. That surface 22 (FIGS. 2A and 4) of plate 20 facing the end cap 18 serves as the impaction surface for Stage I.

A first stage impaction nozzle 25 (FIGS. 2A and 4) is mounted through the end cap 18 concentrically about the sampler axis $A_S$ so that the first stage impaction nozzle 25 extends from outside the end cap 18 into the first stage impaction chamber 21. The first stage impaction nozzle 25 defines a first stage impaction jet passage 26 therethrough which is also concentric about the sampler axis $A_S$. The inlet 28 (FIG. 2A) to the first stage impaction jet passage 26 lies outside the end cap 18 and serves as the inlet $I_S$ to the sampler 10. The inlet 28 is connected either to the outlet $O_P$ of the preseparator 11 or to the inlet nozzle IN. The impaction outlet 29 (FIG. 2A) from the jet passage 26 is located in the vicinity of the first stage impaction surface 22 on the impaction plate 20 to cause the appropriate size particles in the gas stream passing out of the impaction outlet 29 to impact on the first stage impaction surface 22 and be separated from the gas stream. Because this is Stage I, the impaction outlet 29 is located to provide an effective particle cut diameter designed to separate the larger size particles in the particle diameter range being sized by the sampler 10 as will become more apparent. It will be seen that the first stage impaction jet passage 26, as seen in FIG. 2A, has a tapered inlet section 26a and a constant diameter outlet section 26b with the outlet section 26b having a diameter $d_3$ while the impaction outlet 29 is located the distance $d_4$ from the first stage impaction surface 22 on the impaction plate 20 as will become more apparent.

A circular second stage impaction plate 30 (FIGS. 2A and 5) is mounted in the section 16b of side wall 16 a distance $d_5$ downstream of the first stage impaction plate 20 as seen in FIG. 2A. Plate 30 is also oriented normal to the sampler axis $A_S$ and forms a second stage impaction chamber 31 of the diameter $d_{22}$ bounded by side wall 16, first stage impaction plate 20 and second stage impaction plate 30. That surface 32 of the second stage impaction plate 30 facing the first stage impaction plate 20 serves as the impaction surface for Stage II.

A plurality of second stage impaction nozzles 35 (FIGS. 2A, 4 and 5) are mounted through the first stage impaction plate 20 so that the nozzle axes $A_2$ (FIG. 2A) of the nozzles 35 are oriented generally parallel to the sampler axis $A_S$. Each of the second stage impaction nozzles 35 defines a second stage impaction jet passage 36 therethrough which has its inlet 38 (FIGS. 2A and 4) located in the first stage impaction chamber 21 and its impaction outlet 39 (FIG. 2A) located in the second stage impaction chamber 31. The number and location of the second stage impaction nozzles 35 may be varied; however, there are three second stage impaction nozzles 39 illustrated in FIG. 2A which are circumferentially spaced about a circular path $P_I$ concentrically of the sampler central axis $A_S$ as best seen in FIGS. 4 and 5 with the circular path $P_I$ having an effective radius $R_I$ from the sampler axis $A_S$. Thus, it will be seen that the second stage impaction jet passages 36 extend through the first stage impaction plate 20 so that the impaction jet passages 36 provide communication between the first stage impaction chamber 21 and the second stage impaction chamber 31 through which the gas stream passes. While the relative circumferential positions of the second stage jet impaction nozzles 35 may be varied, they are illustrated with the central nozzle 35 radially aligned with the top indicia K and the other nozzles 35 circumferentially spaced on opposite sides thereof along path $P_I$ through angle $A_3$. It will thus be seen that when the sampler 10 is oriented so that its axis $A_S$ is about horizontal, the diametric line $L_V$ (FIGS. 4 and 5) extending through the axis $A_S$ and the central nozzle axis $A_2$ will be about vertical. In this position, all three of the second stage impaction nozzles 35 are located above the horizontal diametric line $L_H$ (FIGS. 4 and 5) extending through axis $A_S$ so that no jet action is associated with the bottom half of the second stage impaction chamber 31 to permit any particles collected in Stage II to fall to the bottom of chamber 31 if they break away from the impaction point on the surface 32 as will become more apparent.

The inlet 38 (FIG. 2A) to each of the second stage impaction nozzles 35 is oriented normal to the nozzle axis $A_2$ and located in the first stage impaction chamber 21 a distance $d_6$ from the first stage impaction surface 22 on plate 20 greater than the distance $d_4$ between the impaction outlet 29 from the first stage impaction nozzle 25 and surface 22. This is to cause the jet stream from the first stage nozzle 25 to have to turn through an angle greater than 180° up to 360° between passage through the first stage nozzle 25 and the second stage nozzle 35 as will become more apparent. The distance $d_6$ is such that the inlets to the second stage impaction nozzles are located from the impaction surface 22 at least as far as the outlet 29 from the first stage nozzle 25 and are illustrated at about 1.7 times the distance $d_4$.

The impaction outlets 39 (FIG. 2A) from the second stage jet passages 36 are all located in the vicinity of the second stage impaction surface 32 on the impaction plate 30 to cause the appropriate size particles in the gas stream passing out of the outlets 39 to impact on the second stage impaction surface 32 and be separated from the gas stream. Because this is Stage II, the impaction outlets 39 are located to provide an effective particle cut diameter designed to separate those particles in the particle diameter range being sized below the effective particle cut diameter of Stage I as will become more apparent. It will be seen that each of the second stage impaction jet passages 36, as seen in FIG. 2A, has a tapered inlet section 36A and a constant diameter outlet section 36b. The outlet section 36b has a diameter $d_8$ while the inlet section 36a tapers inwardly from maximum diameter $d_9$ at inlet 38 down to diameter $d_8$ so that the gas stream is uniformly speeded up to the second stage jet impaction velocity. The second stage impaction outlet 39 is located a distance $d_{10}$ (FIG. 2A) from the impaction surface 32 as will become more apparent.

An exit tube 40 is provided on the second stage impaction plate 30 concentrically about the sampler central axis $A_S$ as seen in FIGS. 2A and 5. The exit tube 40 defines an exit passage 41 therethrough concentrically of the sampler axis $A_S$ so that the inlet end 42 of exit passage 41 is located within the second stage impaction chamber 31 while the outlet end 44 of the exit passage 41 opens into the third stage separation chamber 51. Thus, it will be seen that exit passage 41 extends through the impaction plate 30 to provide communication through the impaction plate 30 from the second stage impaction chamber 31 to the third stage separation chamber 51. Exit tube 40 projects from the second stage impaction plate 30 into the second stage impaction chamber 31 a distance $d_{11}$ above the impaction surface greater than the distance $d_{10}$ between the second stage impaction outlets 30 of the impaction jet passages 36 and the second stage impaction surface 32. The diameter $d_{12}$ of the exit passage 41 is such that the cross-sectional area of the exit passage 41 is at least two times that of the total cross-sectional sectional area of the second stage impaction jet passages 36 and is illustrated as about fourteen times the total cross-sectional area of the outlet sections 36a of jet passages 36. The inlet end 42 of the exit passage 41 is oriented normal to the sample axis $A_S$ at the distance $d_{11}$ which is illustrated at about four times the distance $d_{10}$ between the impaction outlets 39 in the second stage impaction nozzles 35 and the impaction surface 32. Because the inlet end 42 of exit passage 41 is located from the second stage impaction surface 32 farther than the impaction outlets 39 on the second stage impaction nozzles 35, the gas stream will have to turn through an angle greater than 180° up to 360° between passage through the second stage nozzles 35 and the exit tube 40 as will become more apparent.

A cylindrical support member 50 (FIG. 2B) connecting the sections 16b and 16c of side wall 16 forms both the third stage separation chamber 51 with section 16b and the second stage impaction plate 30, and a backup filter stage separation chamber 52 with section 16c and the end plate 19, both of the diameter $d_{23}$. The support member 50 mounts a third stage cyclone separator assembly 55 (FIGS. 2B and 6) thereon which projects into the third stage separation chamber 51 and a backup filter assembly 56 (FIG. 2B) thereon which projects into the backup stage separation chamber 52.

The support member 50 has a threaded boss 60 (FIG. 2B) thereon concentric about sampler axis $A_S$ and projecting into the third stage separation chamber 51. The cyclone housing 51 (FIGS. 2B and 6) of cyclone separator assembly 55 is screwed onto boss 60 so that a cyclone chamber 62 of diameter $d_{14}$ is formed by housing 61 and boss 60. The cyclone chamber 62 follows conventional cyclone design parameters with a cylindrical section 65 at the tengential inlet 64 through housing 61 from the third stage separation chamber 51 to the cyclone chamber 62 and a tapered section 66 through which the separated particles are discharged into the collection chamber 68 in collection cup 69 (FIG. 2B). The cup 69 is removably connected to the opposite end of housing 61 from the boss 60.

The gas exits of chamber 62 through exit passage 70 through the support member 50 (FIG. 2B). The inlet end 71 of the exit passage 70 is spaced in the cyclone chamber 62 a distance $d_{15}$ by a tubular projection 72 on member 50 to provide the cyclonic action to the gas stream passing through the cyclone chamber 62 to separate the particles therefrom. The exit passage 70 has an inlet section 74 of diameter $d_{16}$ and an outlet section 75 of larger diameter $d_{18}$ with a diverging section 76 connecting these sections. The outlet section 75 of the exit passage 70 is partly formed by a tubular projection 78 projecting into the backup filter separation chamber 52 (FIG. 2B).

The backup filter assembly 56 (FIG. 2B) is mounted on the projection 78 about the outlet end 79 of passage 70. The open end of the cup-shaped backup filter 80 fits snugly over projection 78 and is held in place by retaining band 81 so that the gas stream passing out of the exit passage 70 must pass through the filter 80 and then out into the backup filter separation chamber 52. The gas stream then passes out of the sampler 10 through outlet $O_S$ in end plate 19 to the vacuum source seen in FIG. 2B.

PRESEPARATOR

The preseparator 11 best seen in FIGS. 1, 2A and 3 is used with sampler 10 when particle sizes above the acceptance range (normally about 10 microns) are present in the gas stream being sampled. The preseparator 11 includes a generally cylindrical housing 115 defining a generally cylindrical preseparator chamber 116 therein of diameter $d_{PC}$ centered along the preseparator axis $A_P$, opening onto one end of the housing 115 at its full diameter and communicating with the outlet $O_P$ through the opposite end of housing 115 into the inlet $I_S$ of sampler 10. The open end of the housing 115 is closed by a cap 119 which incorporates the preseparator impaction nozzle 120. The outside of housing 115 adjacent the open end is externally threaded to mate with the internal threads on cap 119 so that the cap 119 can be unscrewed from housing 115 to gain access to the preseparator chamber 116.

A circular impaction plate 125 is mounted on the housing 115 within the preimpaction chamber 116 and oriented normal to the preseparator axis $A_P$ to separate the preimpaction chamber 116 into an impaction subchamber 126 facing the cap 119 and a discharge subchamber 128 which communicates with the outlet $O_P$. That surface 129 of plate 125 facing the cap 119 serves as the preimpaction surface onto which the larger size particles in the gas stream are impacted to preseparate them from the gas stream prior to entry into the particle sizing sampler 10.

The preseparator impaction nozzle 120 mounted through cap 119 is arranged concentrically about the preseparator axis $A_P$ and defines a preimpaction jet passage 130 of diameter $d_J$ therethrough also concentric about axis $A_P$ and normal to the preimpaction surface 129. The inlet 131 to the jet passage 130 serves as the inlet $I_P$ to preseparator 11 and is outside the cap 119 to communicate with the gas stream through the pickup nozzle IN. The impaction outlet 134 from the jet passage 130 is located a distance $d_J$ from the impaction surface 129 to cause those larger size particles in the gas stream passing out of the outlet 134 to impact on the surface 129 and be separated from the gas stream as will become more apparent.

A plurality of exit tubes 135 are mounted on the impaction plate 125 so that the exit tube axes $A_E$ are oriented generally parallel to the preseparator central axis $A_P$. The number and location of the exit tubes 135 may be varied; however, there are three exit tubes 135 illustrated in the figures and are circumferentially spaced about a circular path $P_E$ concentrically of the preseparator central axis $A_P$ with the circular path $P_E$ having a radius $R_E$ from axis $A_P$ as best seen in FIG. 3. While the relative circumferential positions of the exit tubes 135 may be varied, they are illustrated with the central exit tube 135 radially aligned with the top indicia K and the other exit tubes 135 circumferentially spaced on opposite sides thereof along path $P_E$ through angle $A_T$. It will thus be seen that when the preseparator 11 is oriented so that its axis $A_P$ is about horizontal, the diametric line $L_V$ extending through the axis $A_E$ will be about vertical. In this position, all three of the exit tubes 135 are located at or above the horizontal diametric line $L_H$ extending through axis $A_P$ so that no significant exit gas flow is associated with the bottom half of the impaction subchamber 26 to permit any particles collected in the preseparator 11 to fall to the bottom of subchamber 26 if they break away from the impaction point on the preimpaction surface 129 as will become more apparent.

Each of the exit tubes 135 defines an exit passage 136 therethrough concentrically of the exit tube axis $A_E$ so that the inlet end 138 of each exit passages 136 is located within the impaction subchamber 126 while the outlet end 139 of the exit passage 136 opens into the discharge subchamber 128. Thus, it will be seen that each exit passage 136 extends through the impaction plate 125 so that the exit passages 136 provide communication through the impaction plate 125 from the impaction subchamber 126 to the discharge subchamber 128. Each of the exit tubes 135 projects from the impaction plate 125 into the impaction subchamber 126 a height $h_E$ as seen in FIG. 2A so that the height $h_E$ is greater than the distance $d_I$ between the impaction outlet 134 of the preimpaction jet passage 130 and the preimpaction surface 129. The diameters $d_{EP}$ of each of the exit passages 136 is such that the total cross-sectional area of the exit passages 136 through the exit tubes 135 is at least two times that of the cross-sectional area of the preimpaction jet passage 130. It will be seen that the diameter $d_{EP}$ of each of the exit passages 136 in the exit tubes 135 is about the same as the diameter $d_J$ of the preimpaction jet passage 130 so that the total cross-sectional area of the exit passages 136 is more than three times the cross-sectional area of the preimpaction jet passage 130. The height $h_E$ of the exit tubes 135 is such that the inlet end 138 of each exit passage 136 is located at least as far from the preimpaction surface 129 as the impaction outlet 134 of the preimpaction jet nozzle 130 and is illustrated at about two times the distance $d_I$.

The particle sizing sampler 10, then, is designed to separate particles from entrainment in a gas stream into classifications according to size. While the sampler 10 may be constructed to handle any desired particle size range, the most common particle size range selected to be sized for classification by the sampler 10 is that particle size range generally considered to be hazardous to the human respiratory system. Such particle size range is commonly accepted as being those particles less than about 10 microns in diameter. The preseparator 11 is used to preseparate those particles with diameters above the particle size range of concern in sample 10. Normally, then, the preseparator 11 placed upstream of the sampler 10 separates those particles from the gas stream whose diameters are above about 10 microns in size.

Figure 7:
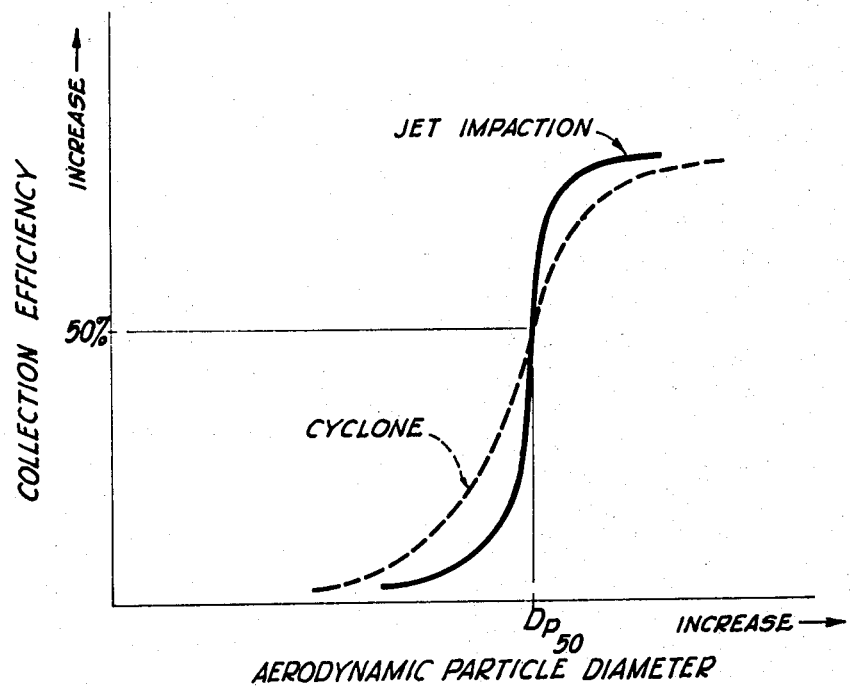
FIG. 7 is a graph showing a typical collection curve for the sampling device.
Figure 8:
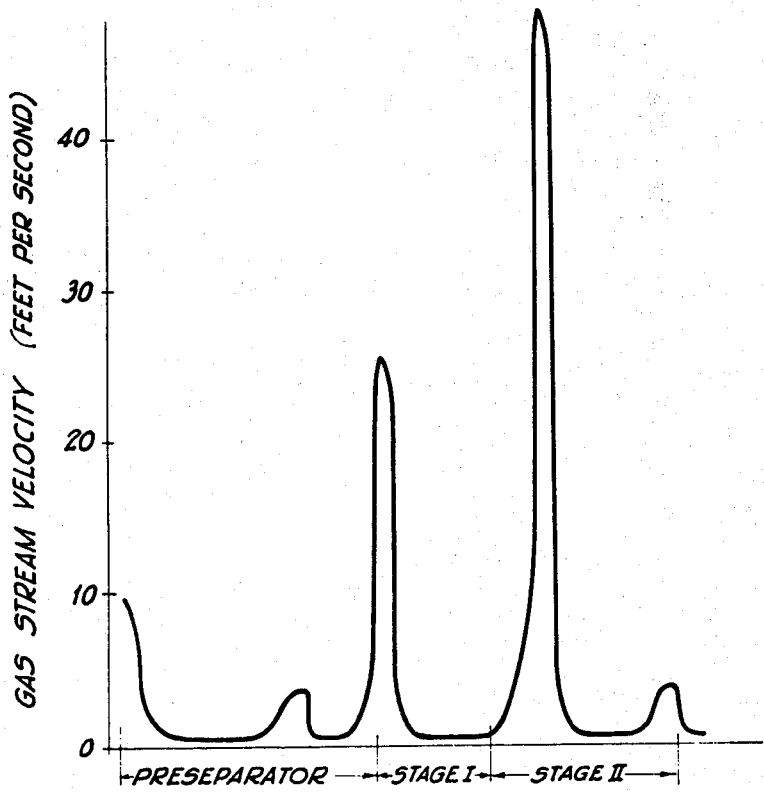
FIG. 8 is a graph illustrating the relative velocity relationships of the gas stream in the invention.
Figure 9:
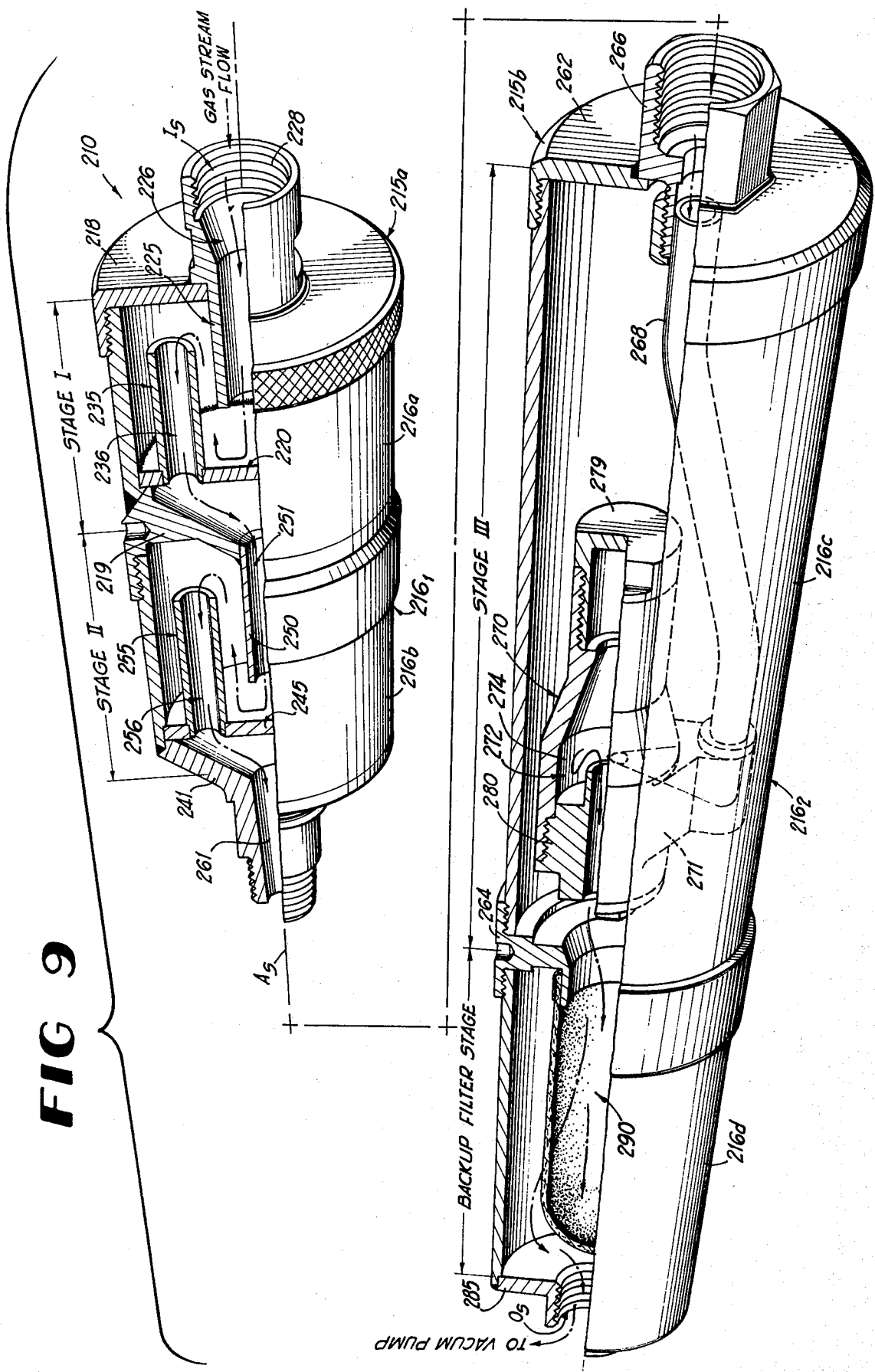
FIG. 9 is an exploded perspective view partially shown in section of a second embodiment of the invention.
Figure 10:
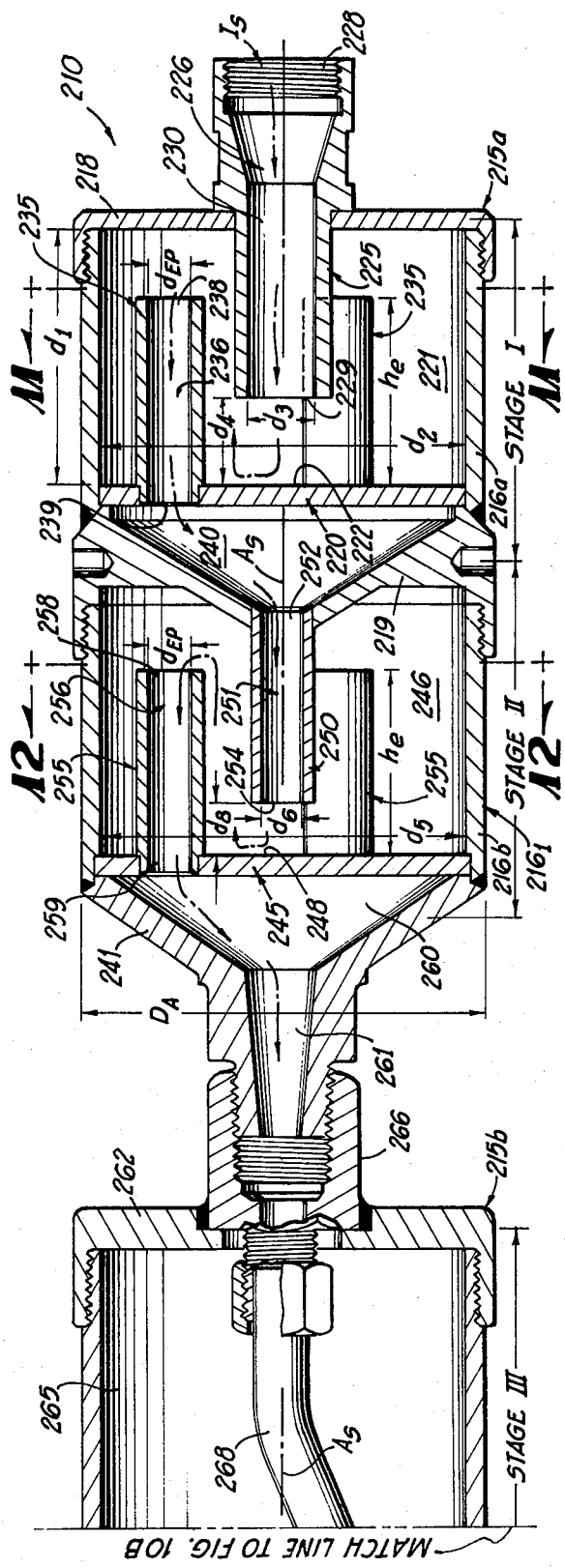
FIGS. 10a and 10b together form an enlarged longitudinal cross-sectional view of that embodiment of the invention in FIG. 9.
Figure 11:
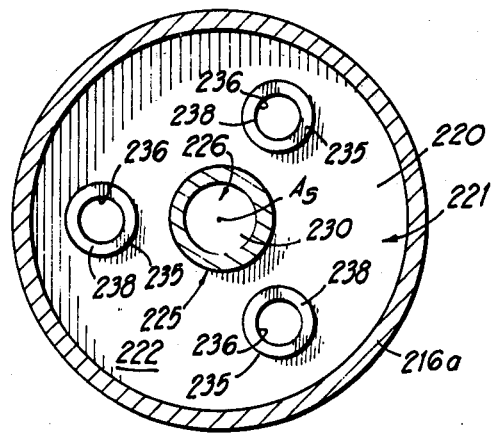
Figure 12:
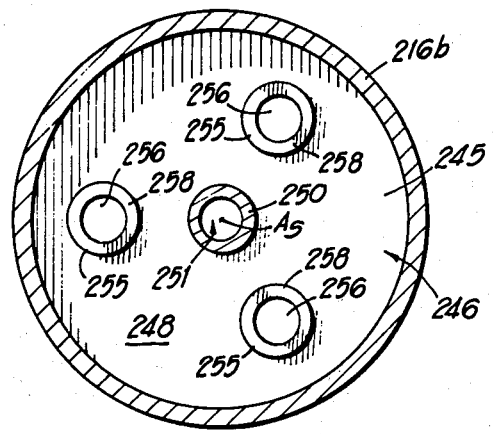
Figure 13:
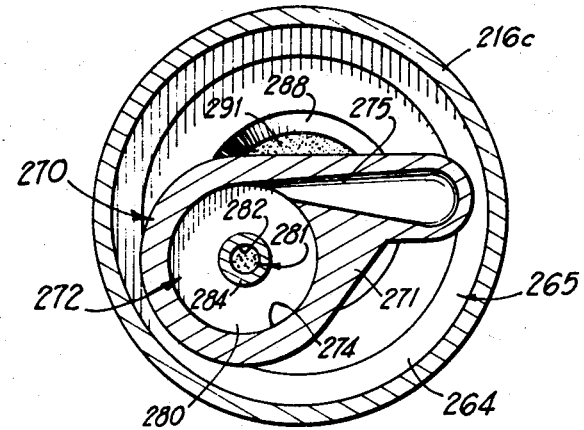

It should also be appreciated what the sampling industry considers as the effective particle cut diameter of a sampling device. Both jet impaction type samplers and cyclone type samplers exhibit similar impaction characteristics. Each stage of such samplers exhibits a generally S-shaped collection efficiency versus particle diameter curve as typified in FIG. 7. The effective particle cut diameter is considered to be that size particle which is collected at a 50% collection efficiency and is referred to as generally by the reference $D_{P50}$. The particle sizes are the effective aerodynamic diameters of the particles and are usually expressed in microns. Normally, the jet impaction collection mechanism produces a collection efficiency curve with a steeper slope in its central section than that of a cyclone type mechanism. This is illustrated in FIG. 7 by showing a typical jet impaction collection efficiency curve in a solid line and a typical corresponding cyclone collection efficiency curve in a dashed line.

While the collection efficiency curves retain about the same general shape, the effective particle cut diameter of a particular stage in sampler 10 or the preseparator can be selected by appropriate selection of the diameter of the jet impaction passage and the distance between the outlet from the jet impaction passage and the impaction surface if such stage is of the jet impaction type or by selecting the diameter of the cyclone chamber if the stage is of the cyclone type. The gas flow rate through the sampling device and the temperature of the gas being sampled also affect the effective particle cut diameter of a sampling device. To compensate for this latter problem, standard flow rate and temperature conditions are selected for use in determining the particular sizes of the sampling device. The standard conditions used in this application are a gas flow rate of about 0.75 acfm (354 cm$^3$/sec.) and a temperature of about 70° F. (21.1° C.); however, other standard conditions may be used. A family of collection efficiency curves is then generated either theoretically or empirically to allow the sampling device to be operated under different gas flow rate and temperature conditions. Generally speaking, a decrease in the gas flow rate through the sampling device causes the effective particle cut diameters to be larger than those for the standard conditions while an increase in gas flow rate causes a reduction in the effective particle cut diameters. Similarly, an increase in gas temperature from the standard conditions generally causes the effective particle cut diameters of the sampling device to be larger than those under standard conditions. The Backup Filter Stage of the sampler 10 is an exception to the above parameters since, being an absolute filter, it will separate virtually all the particles remaining in the gas stream after passage through the other stages of the sampler 10 without regard to gas stream conditions. The various sizes used and described hereinafter in the sampler 10 are designed to provide the effective particle cut diameters discussed at the standard conditions. Normally, a family of curves is generated which allow the preseparator 11 and sampler 10 to be used in conditions other than the standard conditions.

While the preseparator 11 may be designed to separate other different size ranges, the preseparator 11 illustrated is designed to have an effective particle cut diameter of about 11 microns under standard conditions. Thus, particles above the 11 micron cut diameter of the preseparator 11 will be collected thereby while those particles below the 10 micron cut diameter of the preseparator 11 will pass into the particle sizing sampler 10 for further division according to size. While the particle sizing sampler 10 may divide the particles in the gas stream below the 10 micron cut diameter of the preseparator 11 into different size categories, the particle sizing sampler 10 illustrated is designed to have an effective particle cut diameter of about 11 microns for Stage I, an effective particle cut diameter of about 6 microns for Stage II, and an effective particle cut diameter of about 1.5 microns for Stage III with the Backup Filter Stage designed to remove those particles remaining in the gas stream below the 1.5 microns cut diameter when the sampler 10 is operating under standard conditions. Table I at the end of the specification sets forth one set of dimensions which have been found adequate to generate the above operating characteristics under standard conditions.

When the preseparator 11 is being used with the particle sizing sampler 10, the gaseous medium passes into preseparator 11 through the inlet nozzle IN where it is discharged out of the preseparator impaction nozzle 120 to impinge against the preimpaction surface 129 on the impaction plate 125 to separate out the larger particles in the gaseous medium. After impingement against the preimpaction surface 129 on impaction plate 125, the gas stream is deflected outwardly along the preimpaction surface 129 so that the gas stream is deflected about 90° from the original path through the preimpaction nozzle 20. Because the diameter $d_{PC}$ of the preseparator chamber 116 is over six times the diameter $d_J$ of the preimpaction jet passage 130 and the cross-sectional area of the impaction subchamber 26 is over thirty times that of the cross-sectional area of the preimpaction jet passage 130, the deflected jet stream passing along the preimpaction surface 129 on the impaction plate 125 rapidly slows down. Because the gas stream rapidly slows down in the impaction subchamber 126, reentrainment due to particle bounce or to particles being dislodged from the point of impaction is minimized. Eventually, the outwardly deflected gas stream is turned away from the preimpaction surface 129 to move up to the level of the inlet ends 138 of the exit passages 136 in exit tubes 135. The gaseous medium then turns back into the exit passages 138 for passage into the discharge subchamber 128 and then out through the outlet $O_P$ into the inlet of the particle sizing sampler 10. It will be noted that the gas stream turns through a total of approximately 360° between the preimpaction jet passage 130 and the exit passage 136 in exit tubes 135 to insure that the particles impacted on the preimpaction surface 125 are not reentrained in the gas stream. When the preseparator 11 is oriented so that the indicia K is at the top of the preseparator 11 and the preseparator axis $A_P$ is horizontal, any particles which agglomerate at the point of impaction on the preimpaction surface 129 fall into the bottom of the impaction subchamber 126 so as to remove them from the area of major gas flow through the impaction subchamber 126 to prevent reentraiment of any of the agglomerated particles back in the gas stream. These agglomerated particles, then, are effectively prevented from passing into the inlet of the particle sampler 10.

The gaseous medium passing into the inlet $I_S$ of the particle sizing sampler 10 passes into Stage I through the first stage jet passage 26 in the first stage impaction nozzle 25 so that the jet stream impinges against the first stage impaction surface 22 on impaction plate 20 to separate out those particles in the gaseous medium above the effective particle cut diameter of Stage I of the sampler 10. After impingement against the first stage impaction surface 22, the jet stream is deflected outwardly along the impaction surface 22 so that the flow path is deflected about 90° from the first stage jet stream path along the sampler axis $A_S$. Because the diameter $d_2$ of the first stage impaction chamber 21 is over eight times the diameter $d_3$ of the first stage impaction jet passage 26 and the effective cross-sectional area of the first stage impaction chamber 21 is over fifty times that of the cross-sectional area of the first stage impaction jet passage 26, the deflected jet stream passing along the impaction surface 22 on the first stage impaction plate 20 rapidly slows down. As with the preseparator 11, this prevents reentrainment of any particles separated from the gas stream by impaction on the first stage impaction plate 20 due to particle bounce and/or particles shearing away from those particles already collected on the first stage impaction surface 22. Eventually, the outwardly deflected gas stream turns away from the first stage impaction surface 22 to move up to the level of the inlet ends 38 of the second stage impaction jet passages 36 through the second stage impaction nozzles 35. The gaseous medium then turns back into the second stage impaction jet passages 36 for passage into Stage II of the sampler 10. It will be noted that the gas stream turns through the total of 360° between the first stage impaction jet passage 26 and the second stage impaction jet passages 36 to insure that the particles impacted on the first stage impaction surface 22 are not reentrained in the gas stream. Further, when the sampler 10 is located so that the sampler axis $A_S$ is horizontal and the indicia K is at the top of the sampler 10, any particles which agglomerate and fall away from the point of impaction on the first stage impaction surface 22 will fall down into the bottom of the first stage impaction chamber 21 so as to be out of the main gas flow path passing through the first stage impaction chamber 21.

In Stage II, the gas stream passes through the second stage jet passages 36 in the second stage impaction nozzles 35 so that the jet streams impinge against the second stage impaction surfaces 32 on impaction plate 30 to separate out those particles in the gaseous medium above the effective particle cut diameter of Stage II of the sampler 10. After impingement against the second stage impaction surface 32, the jet streams are deflected away from the points of impingement along the impaction surface 32 so that the flow paths are deflected about 90° from the second stage jet stream paths along the nozzle axes $A_2$. Because the diameter $d_{22}$ of the first stage impaction chamber 31 is over nineteen times the diameter $d_8$ of the second stage impaction jet passages 36 and the effective cross-sectional area of the second stage impaction chamber 31 is over ninety times that of the total cross-sectional area of the second stage impaction jet passages 36, the deflected jet streams passing along the impaction surface 32 on the second stage impaction plate 30 rapidly slow down. This prevents reentrainment of any particles separated from the gas stream by impaction on the second stage impaction plate 30 due to particle bounce and/or particles shearing away from those particles already collected on the second stage impaction surface 32. Eventually, the outwardly deflected gas streams turn away from the second stage impaction surface 32 to move up to the level of the inlet end 42 of the exit tube 40 of passage into Stage II of the sampler 10. It will be noted that the gas streams have turned through a total of 360° between the second stage impaction jet passages 36 and the exit passage 41 through exit tube 40 to insure that the particles impacted on the second stage impaction surface 22 are not reentrained in the gas stream. Further, when the sampler 10 is located so that the sampler axis $A_S$ is horizontal and the indicia K is at the top of the sampler 10, any particles which agglomerate and fall away from the points of impaction on the second stage impaction surface 32 will fall down into the bottom of the second stage impaction chamber 31 so as to be out of the main gas flow path passing through the second stage impaction chamber 31. Because the diameter $d_{12}$ of the exit passage 41 is over six times the diameter $d_8$ of any one of the second stage jet impaction passages 36 and the cross-sectional area of the exit passage 41 is over thirteen times the total cross-sectional area of the second stage jet impaction passages 36, the gas stream velocity through exit passage 41 is sufficiently below the velocity in the second stage jet passages 36 to prevent inadvertent particle separation in tube 40.

The gas stream passing into Stage III from the exit passage 41 expands and immediately slows down since the diameter $d_{23}$ of the third stage separation chamber 51 is over three times the diameter $d_{12}$ of passage 41 and the cross-sectional area of chamber 51 is over nine times the cross-sectional area of the exit passage 41. This insures that inadvertent separation of the particles remaining in the gas stream before entry into the cyclone assembly 55 is prevented. This is further insured by locating the closest surface on the cyclone assembly 55 to the outlet 44 of exit passage 41 a distance $d_{19}$ therefrom which is greater than the diameter of passage 41.

The gas stream then passes into the chamber 62 of the third stage cyclone assembly 55 through the tangential inlet 64 to subject the gas stream to cyclonic action in chamber 62. This causes the particles in the gas stream above the effective particle cut diameter of the cyclone assembly 55 to be discharged into the collection chamber 68 in cup 69 for collection. The gas stream passes out of chamber 62 through the exit passage 70 in the member 50. As soon as the gas stream passes through the inlet section 74 whose size helps control the cyclonic action in chamber 62, it expands in the outlet section 75 to slow down.

The gas stream then passes into the inside of the backup filter 80 and out through the sidewall of the filter 80 so that the remaining particles in the gas stream are removed in filter 80. The clean gas stream passes out into the chamber 52 and then out through outlet $O_S$ to the vacuum pump.

The outside diameters $d_{OI}$ and $d_{OII}$ of the first stage nozzle 25 and the second stage nozzles 35 respectively are less than one-third of the diameters $d_2$ and $d_{22}$ of their cooperating impaction chambers 21 and 31 so that the jet streams from the nozzles 25 and 35 are free to expand both outwardly and back up away from the point of impaction to provide the quickest practical slowing of the gas stream velocity to reduce the likelihood of reentrainment. Further, the jet streams from the nozzles 35 in Stage II are located at least three passage diameters $d_8$ apart to prevent reentrainment due to adjacent jet stream interference.

The preseparator 11 and those portions of the sampler 11 using a jet impaction collection mechanism are characterized by the gas stream velocity in each slowing by a factor of at least ten in the impaction chamber substantially immediately after impaction and not rising above a velocity of about one-half the jet impaction velocity as the gas stream exits the impaction chamber. It is this combination of drastically slowing and then gradually reincreasing the gas stream velocity that assures minimization of reentrainment problems. Another factor which affects the particle separation of the gas stream is the residence time of the gas stream in the impaction chamber. This is especially true with impacted particles which agglomerate after separation from the gas stream and are then broken away from the point of impaction by the impaction jet action. The residence time of the gas stream in the impaction chamber must be sufficiently long to permit the agglomerated particles to settle out of the gas stream when they break away. This time should be a minimum of about 0.20 second and is illustrated under standard operating conditions at a much longer time as indicated in Table I.

It will be appreciated that the number of jet impaction nozzles increases as the jet velocity increases to decrease the likelihood of particle shear problems. It has been found that a single nozzle can handle impaction jet stream velocities of up to about 25–30 feet per sec. (7.62–9.14 meters per sec.). The number of impaction nozzles should increase by a factor of about 1.5 multiplied times the factor by which this base impaction velocity increases. For example, the impaction velocity of Stage II is about two times the base impaction velocity and thus needs three impaction nozzles as shown.

TABLE I

| Stage I: | |
|---|---|
| Chamber diameter $d_2$ | 2.5 in. (6.35 cm) |
| Jet Passage diameter $d_3$ | 0.48 in. (1.22 cm.) |
| Impaction distance $d_4$ | 0.59 in. (1.50 cm) |
| Exit height $d_6$ | 1.19 in. (3.02 cm) |
| Exit diameter $d_9$ | 0.44 in. (1.12 cm) |
| Under standard conditions of | 0.75 acfm and 70° F.: |
| Jet velocity | 9.75 fps (2.97 mps) |
| Chamber velocity | 0.44 fps (0.13 mps) |
| Exit velocity | 3.92 fps (1.19 mps) |
| Cut diameter $Dp_{50}$ | 11.0 microns |
| Stage II: | |
| Chamber diameter $d_{22}$ | 2.56 in. (6.50 cm) |
| Jet passage diameter $d_8$ | 0.30 in. (0.76 cm) |
| Impaction distance $d_{10}$ | 0.63 in. (0.91 cm) |
| Exit height $d_{11}$ | 1.00 in. (2.54 cm) |
| Exit diameter $d_{12}$ | 0.50 in. (1.27 cm) |
| Under standard conditions of | 0.75 acfm and 70° F.: |
| Jet velocity | 25.5 fps (7.77 mps) |
| Chamber velocity | 0.49 fps (0.15 mps) |
| Exit velocity | 3.64 fps (1.11 mps) |
| Cut diameter $Dp_{50}$ | 6 microns |

SECOND EMBODIMENT

Referring to FIGS. 9–14, a second embodiment of the sampler is illustrated and designated generally by numeral 210. The sampler 210 has a sampler central axis $A_S$, an inlet $I_S$ and outlet $O_S$. Normally, the sampler outlet $O_S$ is connected to a vacuum pump as is well known in the sampler art while the inlet $I_S$ of the sampler 210 is generally connected to an appropriate inlet nozzle. When the sampler 210 is inserted into the gas stream, the inlet opening of the inlet nozzle faces the oncoming gas stream with its inlet axis generally parallel to the gas stream flow. The sample of the gaseous medium taken in through the inlet nozzle passes generally axially through the sampler 210 and then out through the vacuum pump.

The particle sizing sampler 210 is designed to divide those size particles entrained in the gaseous medium similarly to sampler 10. The particle sizing sampler 210, then, separates those particles which lie generally below the 11 micron size range according to size. The particle sizing sampler 210 may have any desired number of stages; however, the particle sizing sampler illustrated has four stages: Stage I, Stage II, Stage III, and a Backup Filter Stage. Under standard operating conditions, as will become more apparent, Stage I is designed to have an effective particle cut diameter of about 11 microns; Stage II is designed to have an effective particle cut diameter of about 6 microns; Stage III is designed to have an effective particle cut diameter of about 1.5 microns; and the Backup Filter Stage is designed to remove all of the particles remaining in the gas stream after passage through Stage III. Stages I and II operate by jet impaction while Stage III is a cyclone and the Backup Stage is an absolute filter. Stage III could likewise operate by jet impaction.

The particle sizing sampler 210 includes generally a pair of cylindrical housings $215_a$ and $215_b$ which mount the four stages of the sampler. The cylindrical housing $215_a$ includes generally a tubular cylindrical side wall $216_1$ which a divided into sections $216_a$ and $216_b$ that are selectively threaded together so that Stages I and II can be disassembled to permit the collected sample to be examined. The cylindrical housing $215_b$ likewise includes a tubular side wall $216_2$ which is divided into sections $216_c$ and $216_d$ that are selectively threaded together so that Stage III and the Backup Filter Stage can be disassembled to permit the collected sample to be examined. It is to be understood, however, that the sampler housing $215_a$ and $215_b$ may be appropriately made as a single unit so that the stages all fit within the common sampler housing without having to disassemble the side walls. The housings $215_a$ and $215_b$ have a maximum transverse cross-sectional diameter $D_A$ sized so that the housings $215_a$ and $215_b$ will pass through the standard access ports conventionally provided in the ducts carrying the gaseous medium. This standard size is usually about 3 inches (7.62 cm) for the access ports so that diameter $D_A$ is less than 3 inches (7.62 cm).

Stage I is mounted on side wall section $216_a$. Stage I is formed by closing the upstream end of side wall section $216_a$ with an inlet end cap 218 and closing the downstream end of side wall section $216_a$ with an intermediate end cap 219 to form a closed chamber bounded thereby. A circular first stage impaction plate 220 (FIGS. 10A and 11) is mounted in this chamber a distance $d_1$ (FIG. 10A) downstream of end cap 218. Plate 220 is oriented normal to the sampler axis $A_S$ and forms a first stage impaction chamber 221 of diameter $d_2$ (FIG. 11) bounded by side wall section $216_a$, end cap 218 and plate 220. That surface 222 (FIGS. 10A and 11) of plate 220 facing the end cap 218 serves as the impaction surface for Stage I.

A first stage impaction nozzle 225 (FIGS. 10A and 11) is mounted through the end cap 218 concentrically about the sampler axis $A_S$ so that the first stage impaction nozzle 225 extends from outside the end cap 218 into the first stage impaction chamber 221. The first stage impaction nozzle 225 defines a first stage impaction net passage 226 therethrough which is also concentric about the sampler axis $A_S$. The inlet 228 (FIG. 10A) to the first stage impaction jet passage 226 lies outside the end cap 218 and serves as the inlet $I_S$ to the sampler 210. The inlet 228 is connected to an inlet nozzle such as that used with sampler 10. The impaction outlet 229 (FIG. 10A) from the jet passage 226 is located in the vicinity of the first stage impaction surface 222 on the impaction plate 220 to cause the appropriate size particles in the gas stream passing out of the impaction outlet 229 to impact on the first stage impaction surface 222 and be separated from the gas stream. Because this is Stage I, the impaction outlet 229 is located to provide an effective particle cut diametr designed to separate the larger size particles in the particle diameter range being sized by the sampler 210 similarly to that of sampler 10. It will be seen that the first stage impaction jet passage 226, as seen in FIG. 10A, has a tapered inlet and a constant diameter main section 230 with the section 230 having a diameter $d_3$ while the impaction outlet 229 is located the distance $d_4$ from the first stage impaction surface 222 on the impaction plate 220 as will become more apparent.

A plurality of exit tubes 235 are mounted on the impaction plate 220 so that the exit tube axes $A_E$ are oriented generally parallel to the sampler central axis $A_S$. The number and location of the exit tubes 235 may be varied; however, there are three exit tubes 235 illustrated in the figures and are equally spaced circumferentially about a circular path $P_E$ concentrically of the sampler central axis $A_S$ with the circular path $P_E$ having a radius $R_E$ from axis $A_S$ as best seen in FIG. 10A.

Each of the exit tubes 235 defines an exit passage 236 therethrough concentrically of the exit tube axis $A_E$ so that the inlet end 238 of each exit passage 236 is located within the impaction chamber 221 while the outlet end 239 of the exit passage 236 opens into the discharge subchamber 240 downstream of the first stage impaction plate 220. Thus, it will be seen that each exit passage 236 extends through the impaction plate 220 so that the exit passages 236 provide communication through the impaction plate 220 from the impaction chamber 221 to the discharge subchamber 240. Each of the exit tubes 235 projects from the impaction plate 220 into the impaction chamber 221 a height $h_E$ as seen in FIG. 10A so that the height $h_E$ is greater than the distance $d_1$ between the impaction outlet 229 of the first stage impaction jet passage 226 and the impaction surface 222. The diameters $d_{EP}$ of each of the exit passages 236 is such that the total cross-sectional area of the exit passages 236 through the exit tubes 235 is at least two times that of the cross-sectional area of the jet passage 226. It will be seen that the diameter $d_{EP}$ of each of the exit passages 236 in the exit tubes 235 is about the same as the diameter $d_3$ of the jet passage 226 so that the total cross-sectional area of the exit passages 236 is more than three times the cross-sectional area of the jet passage 226. The height $h_E$ of the exit tubes 235 is such that the inlet end 238 of each exit passage 236 is located at least as far from the impaction surface 222 as the impaction outlet 229 of the first stage jet nozzle 225 and is illustrated at about two times the distance $d_1$. The gas stream then passes from the discharge subchamber 240 into Stage II.

Stage II is mounted on side wall section $216_b$. Stage II is formed by using the intermediate end cap 219 to close the upstream end of side wall section $216_b$ while intermediate discharge end cap 241 closes the downstream end thereof to form a second chamber in the housing $215_a$. A circular second stage impaction plate 245 (FIGS. 10A and 12) is mounted in this chamber a distance $d_5$ downstream of the intermediate end cap 219 as seen in FIG. 10A. Plate 245 is also oriented normal to the sampler axis $A_S$ and forms a second stage impaction chamber 246 of the diameter $d_5$ bounded by side wall section $216_b$, intermediate end cap 219 and second stage impaction plate 245. That surface 248 of the second stage impaction plate 245 facing the intermediate end cap 219 serves as the impaction surface for Stage II.

A second stage impaction nozzle 250 (FIGS. 10A and 12) is mounted through the intermediate end cap 219 concentrically about the sampler axis $A_S$ so that the second stage impaction nozzle 250 extends from discharge subchamber 240 into the second stage impaction chamber 246. The second stage impaction nozzle 250 defines a second stage impaction jet passage 251 therethrough which is also concentric about the sampler axis $A_S$. The inlet 252 (FIG. 10A) to the second stage impaction jet passage 251 lies inside discharge subchamber 240 while the impaction outlet 254 (FIG. 10A) from the jet passage 251 is located in the vicinity of the second stage impaction surface 248 on the impaction plate 245 to cause the appropriate size particles in the gas stream passing out of the impaction outlet 254 to impact on the second stage impaction surface 248 and be separated from the gas stream. Because this is Stage II, the impaction outlet 254 from nozzle 250 is located to provide an effective particle cut diameter designed to separate the particles in the gas stream in the next particle diameter range down from Stage I similarly to Sampler 10. The jet passage 251 has a diameter $d_6$ while the impaction outlet 254 therefrom is located the distance $d_8$ from the second stage impaction surface 248 on plate 245 as will become more apparent.

A plurality of exit tubes 255 are mounted on the second stage impaction plate 245 so that the exit tube axes $A_E$ are oriented generally parallel to the sampler central axis $A_S$. The number and location of the exit tubes 235 may be varied; however, there are three exit tubes 235 illustrated in the figures and are equally spaced circumferentially about a circular path $P_E$ concentrically of the sampler central axis $A_S$ with the circular path $P_E$ having a radius $R_E$ from axis $A_S$ as best seen in FIG. 10A.

The second stage exit tubes 255 correspond to those in Stage I with an exit passage 256 through each along the exit tube axis $A_E$ so that the inlet end 258 to each is located in the second stage impaction chamber 246 while the outlet end 259 is located in the second stage discharge subchamber 260 downstream of the second stage impaction plate 245. Like each of the exit tubes in Stage I, exit tubes 255 project into the second stage impaction chamber 246 the height $h_E$ from plate 245 and passages 256 therethrough have diameter $d_{EP}$. Thus, the total cross-sectional area of the passages 256 is about eight times that of the second stage impaction passage 251 and the height $h_E$ thereof is about four times distance $d_6$. The gas stream passes out of the subchamber 260 into the housing $215_b$ carrying Stage III through discharge passage 261 in the end cap 241.

The particle sizing sampler 210, then, is designed to separate particles from entrainment in a gas stream into classifications according to size similarly to sampler 10. While the sampler 210 may be constructed to handle any desired particle size range, the most common particle size range selected to be sized for classification by the sampler 210 is that particle size range, usually less than 10 microns, generally considered to be hazardous to the human respiratory system. The particle sizing sampler 210, like sampler 10, is designed to have an effective particle cut diameter of about 11 microns for Stage I, an effective particle cut diameter of about 6 microns for Stage II, and an effective particle cut diameter of about 1.5 microns for Stage III with the Backup Filter Stage designed to remove those particles remaining in the gas stream below the 1.5 micron cut diameter when the sampler 210 is operating under standard conditions. Table II at the end of the specification sets forth one set of dimensions which have been found adequate to generate the above operating characteristics under standard conditions.

TABLE II

| Stage I | |
|---|---|
| Chamber diameter $d_2$ | 2.5 in. (6.35 cm) |
| Jet Passage diameter $d_3$ | 0.48 in. (1.22 cm) |
| Impaction distance $d_4$ | 0.62 in. (1.57 cm) |
| Exit height $h_E$ | 1.30 in. (3.30 cm) |
| Exit diameter $d_{EP}$ | 0.44 in. (1.12 cm) |
| Under standard conditions of | 0.75 acfm and 70° F.: |
| Jet Velocity | 9.75 fps (2.97 mps) |
| Chamber Velocity | 0.44 fps (0.13 mps) |
| Exit Velocity | 3.92 fps (1.19 mps) |
| Cut diameter $Dp_{50}$ | 11.00 microns |
| Stage II | |
| Chamber diameter $d_5$ | 2.56 in. (6.50 cm) |
| Jet passage diameter $d_6$ | 0.28 in. (0.71 cm) |
| Impaction distance $d_8$ | 0.37 in. (0.93 cm) |
| Exit height $h_E$ | 1.30 in. (3.30 cm) |
| Exit diameter $d_{EP}$ | 0.44 in. (1.12 cm) |
| Under standard conditions of | 0.75 acfm and 70° F.: |
| Jet Velocity | 22.2 fps (6.76 mps) |
| Chamber Velocity | 0.49 (0.15 mps) |
| Exit Velocity | 3.92 fps (1.20 mps) |

TABLE II-continued

| | |
|---|---|
| Cut diameter $Dp_{50}$ | 6 microns |

What is claimed as invention is:

1. A multiple stage particle sizing sampling device for separating particles from a gaseous medium according to particle diameter so as to classify the particles as the gaseous medium is forced therethrough, said sampling device including first and second stages and comprising:
a housing defining a first stage impaction chamber and a second stage impaction chamber therein, both oriented about a common central axis;
impaction means including a first stage impaction member defining a first stage impaction surface thereon in said first stage impaction chamber oriented generally normal to the central axis, and a second stage impaction member defining a second stage impaction surface thereon in said second stage impaction chamber oriented generally normal to the central axis;
impaction nozzle means including a first stage impaction nozzle operatively associated with said first stage impaction chamber and a plurality of second stage impaction nozzles operatively associated with said second stage impaction chamber, said first stage impaction nozzle defining a first stage impaction jet passage therethrough oriented normal to said first stage impaction surface and having a first stage jet inlet thereto and the first stage jet outlet therefrom, said first stage jet inlet in communication with the gaseous medium to be sampled and said first stage jet outlet sized and located with respect to said first stage impaction surface to cause particles in the gaseous medium to be separated by jet impaction on said first stage impaction surface within said first stage impaction chamber so that said first stage has a first prescribed effective particle cut diameter when the gaseous medium is forced through said first stage impaction jet passage; each of said second stage impaction nozzles defining a second stage impaction jet passage therethrough oriented generally normal to said second stage impaction surface having a second stage jet inlet thereto and a second stage jet outlet therefrom, said second stage jet inlet in communication with the gaseous medium in said first stage impaction chamber and said jet outlet sized and located with respect to a second stage impaction surface to cause particles in the gaseous medium to be separated by jet impaction on said second stage impaction surface within said second stage impaction chamber so that second stage has a second prescribed effective particle cut diameter smaller than said first prescribed effective particle cut diameter when the gaseous medium is forced through said second stage impaction jet passages, said second stage impaction jet passages through said second stage impaction nozzles providing communication between said first stage impaction chamber and said second stage impaction chamber so that the gaseous medium moves from said first stage impaction chamber into said second stage impaction chamber through said second stage impaction jet passages, said second stage jet inlets located in said first stage impaction chamber and spaced from said first stage impaction surface a first exit distance greater than the distance between said first stage jet outlet from said first stage impaction jet nozzle and said first stage impaction surface; the size of said first stage impaction chamber, the first exit distance and the total cross-sectional area of said second stage jet inlets being such that the velocity of the gaseous medium through said first stage impaction chamber is less than one-tenth the velocity of the gaseous medium through said first stage jet outlet to permit the particles that bounce from said first stage impaction surface upon impaction to be collected out of the gaseous medium within said first stage impaction chamber, being such that the velocity of the gaseous medium passing out of said first stage impaction chamber through said second stage jet inlets is less than one-half the velocity of the gaseous medium through said first stage jet outlet to prevent the motion of the gaseous medium flowing out of said first stage impaction chamber into said second stage jet inlets from dislodging and re-entraining particles which have already been separated in said first stage impaction chamber, and being such that the residence time of the gaseous medium in said first stage impaction chamber is at least 0.2 second to permit agglomerated particles dislodged after separation in said first stage impaction chamber to settle out of the gaseous medium as it flows through said first stage impaction chamber; and at least one second stage exit tube defining an exit passage therethrough having a second stage exit passage inlet thereto in communication with said second stage impaction chamber and a second stage exit passage outlet therefrom, said second stage exit passage inlet located in said second stage impaction chamber and spaced from said second stage impaction surface a second exit distance greater than the distance between said second stage jet outlets from second stage impaction jet nozzles and said second stage impaction surface; the size of said second stage impaction chamber, the second exit distance and the total cross-sectional area of said second stage exit passage inlet being such that the velocity of the gaseous medium through said second stage impaction chamber is less than one-tenth the velocity of the gaseous medium through said second stage jet outlets into said second stage impaction chamber to permit the particles that bounce from said second stage impaction surface upon impaction to be collected out of the gaseous medium within said second stage impaction chamber, being such that the velocity of the gaseous medium passing out of said second stage impaction chamber through said second stage exit passage inlet is less than one-half the velocity of the gaseous medium through said second stage jet outlets to prevent the motion of the gaseous medium flowing out of said second stage impaction chamber into said second stage exit passage inlet from dislodging and re-entraining particles which have already been separated in said second stage impaction chamber, and being such that the residence time of the gaseous medium in said second stage impaction chamber is at least 0.2 second to permit agglomerated particles dislodged after separation in said second stage impaction chamber to settle out of the gaseous medium as it flows through said second stage impaction chamber.

2. The particle sizing sampling device of claim 1 wherein said sampling device further includes a third stage;

wherein said housing further defines a third stage separation chamber therein oriented about the central axis; and wherein said third stage includes a cyclone mounted in said third stage separation chamber, said cyclone defining a cyclone chamber therein, a cyclone outlet from said cyclone chamber and a cyclone inlet to said cyclone chamber communicating with said second stage exit passage outlet so that the gaseous medium passes from said second stage impaction chamber into said cyclone chamber through said cyclone inlet, said cyclone constructed and arranged to cause particles in the gaseous medium to be separated from the gaseous medium by cyclonic action in said cyclone so that said third stage has a third prescribed effective particle cut diameter smaller than said second prescribed effective particle cut diameter.

3. The particle sizing sampling device of claim 1 wherein said sampling device further includes a backup filter stage;

wherein said housing further defines a backup separation chamber therein;

said backup filter stage including a backup filter communicating with said cyclone outlet so that the gaseous medium passing from said cyclone chamber passes through said backup filter so that the particles remaining in the gaseous medium after passage through said cyclone are separated from the gaseous medium.

4. A multiple stage particle sizing sampler for separating particles from a gaseous medium forced therethrough including a plurality of interconnected impaction stages through which the gaseous medium is serially passed to separate different size particles from the gas stream in each stage, each of said impaction stages comprising:

an impaction chamber having an impaction surface forming one end thereof;

an impaction nozzle defining an impaction jet passage therethrough through which the gaseous medium is forced into said impaction chamber, said impaction jet passage sized and located with respect to said impaction surface to cause the gaseous medium to impinge against the impaction surface with a prescribed impaction velocity so that particles in the gaseous medium are separated by jet impaction on said impaction surface within said impaction chamber when the gaseous medium is forced through said impaction jet passage where the prescribed effective particle cut diameter of each stage is less than the prescribed effective particle cut diameter of the stage immediately upstream thereof; and a plurality of exit tubes projecting into said impaction chamber from said impaction surface for a prescribed exit distance, each of said exit tubes defining an exit passage therethrough having an inlet thereto at that end of the exit tube projecting into said impaction chamber so that the gaseous medium exits said impaction chamber through said exit passages; the relative sizes of said impaction jet passage and said impaction chamber selected so that the velocity of the gaseous medium passing through said impaction chamber is no greater than one-tenth of the velocity of the gaseous medium passing from said impaction jet passage to permit the particles that bounce from said impaction surface upon impaction to be collected out of the gaseous medium within said impaction chamber, the relative cross-sectional sizes of said inlets to said exit passages and said impaction jet passage selected so that the velocity of the gaseous medium through said inlets to said exit passages is no greater than one-half of the velocity of the gaseous medium passing from said impaction jet passage to prevent the motion of the gaseous medium flowing from said impaction chamber into said inlets to said exit passages from dislodging and re-entraining particles which have already been separated in said impaction chamber, and said exit distance between said inlets to said exit passages and said impaction surface together with the cross-sectional size of said impaction chamber selected so that the residence time of the gaseous medium in said impaction chamber is at least 0.2 second at the volumetric gas flow rate at which the stage is operated to permit agglomerated particles dislodged after separation to settle out of the gaseous medium as it flows through said impaction subchamber, said impaction jet passage of the upstreammost of said impaction stages communicating with the gaseous medium to be sampled and said impaction jet passage of each of said impaction stages downstream of said upstreammost impaction stage communicating with the gaseous medium passing out of said exit tubes of said impaction stage immediately upstream thereof.

5. The multiple stage particle sizing chamber of claim 4 wherein said sampler further includes a cyclone stage, said cyclone stage including a cyclone defining a cyclone chamber therein, a cyclone outlet from said cyclone chamber and a cyclone inlet to said cyclone chamber communicating with the gaseous medium passing out of said exit passages in said exit tubes of the downstreammost of said impaction stages so that the gaseous medium passes from said exit tubes in said downstreammost impaction stage into said cyclone chamber through said cyclone inlet, said cyclone constructed and arranged to cause particles in the gaseous medium to be separated from the gaseous medium by cyclonic action in said cyclone where the effective particle cut diameter of said cyclone stage is smaller than that of said downstreammost impaction stage.

6. The multiple stage particle sizing sampler of claim 5 wherein said sampler further includes a backup filter stage, said backup filter stage including a backup filter communicating with said cyclone outlet so that the gaseous medium passing from said cyclone chamber passes through said backup filter to separate any particles remaining in the gaseous medium after passage through said cyclone from the gaseous medium.

7. The multiple stage particle sizing sampler of claim 6 wherein said exit tubes in each of said impaction stages are oriented generally parallel to said impaction jet passage and each of said exit tubes is spaced from said impaction nozzle by a center-to-center distance greater than the diameter of said impaction jet passage to prevent said exit tubes from affecting the jet impaction characteristics of the gaseous medium impacting on said impaction surface.

8. The multiple stage particle sizing sampler of claim 7 wherein said impaction nozzle and said exit tubes in each of said impaction stages are arranged to cause the gaseous medium to undergo a shift in flow direction greater than 180° from passage through said jet impaction passage to passage through said exit passages in said exit tubes.

9. The multiple stage particle sizing sampler of claim 8 wherein the net cross-sectional area of said impaction chamber in each of said impaction stages is at least twenty times the cross-sectional area of said impaction jet passage for that stage.

10. The multiple stage particle sizing sampler of claim 9 wherein said exit passages through said exit tubes in each of said impaction stages have a combined cross-sectional area at least 2.5 times the cross-sectional area of said impaction jet passage for that stage.

11. The multiple stage particle sizing sampler of claim 4 wherein said prescribed exit distance in each of said impaction stages is at least two times the distance between the outlet from said impaction jet passage and said impaction plate; and wherein the relative sizes of said impaction jet passage and said impaction chamber in each of said impaction stages are selected so that the velocity of the gaseous medium passing through said impaction chamber is no greater than one-twentieth of the velocity of the gaseous medium passing from said impaction jet passage.

12. A method of separating particles from gas streams according to particle diameter range so as to classify the particles according to size comprising the steps of:

(a) sequentially passing the gas stream serially through a plurality of impaction sampler stages where each impaction sampler stage has an effective particle cut diameter smaller than the sampler stage immediately upstream thereof; and (b) in each of the impaction sampler stages, impinging the gas stream against an impaction surface in an impaction chamber at a jet velocity such that particles in the gas stream are separated from the gas stream by jet impaction on the impaction surface os that the impactiion sampler stage has a prescribed effective particle cut diameter; substantially immediately after impingement of the gas stream against the impaction surface, allowing the velocity of the gas stream in the impaction chamber to slow to a velocity less than one-tenth the jet velocity of the gas stream to permit the particles that bounce from the impaction surface upon impaction to be collected out of the gaseous medium within the impaction chamber; moving the gas stream away from the impaction surface in a direction opposite to the direction of movement as the gas stream moves toward impingement on the impaction surface for a distance greater than the distance the gas stream moves toward the impaction surface while unconfined so that the residence time of the gaseous medium in the impaction chamber is at least 0.2 second to permit agglomerated particles dislodged after separation to settle out of the gaseous medium as it flows through the impaction chamber; and then moving the gas stream out of the impaction chamber at a velocity less than one-half the jet velocity of the gas stream to prevent the motion of the gaseous medium flowing from the impaction chamber from dislodging and re-entraining particles which have already been separated in the impaction chamber.

13. The method of claim 12 wherein step (b) further includes allowing the velocity of the gas stream in each of the sampler stages to slow to a velocity of about 0.4 feet per second in the impaction chamber after impingement against the impaction surface and moving the gas stream out of the impaction chamber at a velocity of about 4 feet per second when the volume flow rate of the gas stream through the sampler stage is about 0.75 cubic feet per minute.

* * * * *

Disclaimer 4,274,846.—*Michael L. Smith*, Atlanta, Ga. PARTICLE SIZING SAMPLER. Patent dated June 23, 1981. Disclaimer filed Jan. 25, 1982, by the assignee, *Andersen Samplers, Inc.*

Hereby enters this disclaimer to all claims of said patent.

[*Official Gazette March 23, 1982.*]